United States Patent [19]

Krüger et al.

[11] Patent Number: 4,515,619
[45] Date of Patent: May 7, 1985

[54] 1,2,3-THIADIAZOLE-5-YL-UREA DERIVATIVES, AGENTS CONTAINING THESE COMPOUNDS WITH PLANT GROWTH REGULATING AND DEFOLIATING ACTIVITY

[75] Inventors: Hans-Rudolf Krüger; Friedrich Arndt; Reinhard Rusch, all of Berlin, Fed. Rep. of Germany

[73] Assignee: Schering Aktiengesellschaft, Berlin and Bergkamen, Fed. Rep. of Germany

[21] Appl. No.: 424,990

[22] Filed: Sep. 27, 1982

[30] Foreign Application Priority Data

Oct. 1, 1981 [DE] Fed. Rep. of Germany ....... 3139505

[51] Int. Cl.³ .................... C07D 285/06; A01N 43/82
[52] U.S. Cl. ......................................... 71/90; 548/127
[58] Field of Search ........................... 548/127; 71/90

[56] References Cited

U.S. PATENT DOCUMENTS 4,340,742 7/1982 Kruger ................................ 548/255
4,358,596 11/1982 Kruger ................................ 548/127

Primary Examiner—Robert Gerstl
Attorney, Agent, or Firm—Michael J. Striker

[57] ABSTRACT

New 1,2,3-thiadiazole-5-yl-urea derivatives as plant growth regulating agents are provided, including processes for producing and using these compounds. The new 1,2,3-thiadiazole-5-yl-urea derivatives have the formula

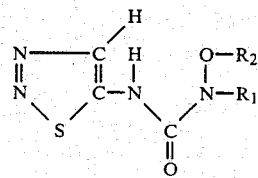

in which $R_1$ is an aromatic hydrocarbon group which may be substituted with one or more members of the group consisting of $C_1$–$C_6$-alkyl, halogen, $C_1$–$C_6$-alkoxy, nitro and trifluoromethyl and $R_2$ is hydrogen, a monovalent metal or its metal equivalent, a substituted or unsubstituted $C_1$–$C_6$-alkyl, a $C_3$–$C_6$-alkenyl or alkinyl, a substituted or unsubstituted aryl- $C_1$–$C_2$-alkyl or the group aryl-$C_1$–$C_2$-alkyl

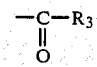

wherein $R_3$ is hydrogen, a substituted or unsubstituted $C_1$–$C_{10}$-alkyl, $C_2$–$C_6$-alkenyl, a $C_2$–$C_6$-alkenyl, an aryl-$C_1$–$C_2$-alkyl, a $C_3$–$C_8$-cycloaliphatic hydrocarbon group which may be substituted with one or more $C_1$–$C_6$-alkyl substituents, an aromatic hydrocarbon group which may be substituted with at least one of $C_1$–$C_6$-alkyl, halogen, $C_1$–$C_6$-alkoxy, nitro and trifluoromethyl, a substituted or unsubstituted heterocyclic hydrocarbon, $C_1$–$C_6$-alkoxy, $C_3$–$C_6$-alkenyl-or alkinyloxy, a substituted or unsubstituted aryloxy, and $C_1$–$C_4$-alkylthio or an arylthio or an amino group

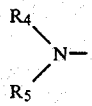

wherein $R_4$ and $R_5$ are each the same or different and are selected from the group consisting of hydrogen, $C_1$–$C_6$-alkyl, aryl or aryl substituted with one or more of the members selected from the group consisting of $C_1$–$C_6$-alkyl, halogen, $C_1$–$C_6$-alkoxy, nitro and trifluoromethyl.

30 Claims, No Drawings

1,2,3-THIADIAZOLE-5-YL-UREA DERIVATIVES, AGENTS CONTAINING THESE COMPOUNDS WITH PLANT GROWTH REGULATING AND DEFOLIATING ACTIVITY

This invention relates to new 1,2,3-thiadiazole-5-yl-urea derivatives, processes for making these compounds, agents having plant growth regulating and defoliating properties based on these compounds and methods of using these compounds.

1,2,3-Thiadiazole-5-yl-urea derivatives having plant growth regulating and defoliating properties are already known (DE-OS Nos. 2,214,632; DE-OS 2,506,690). In spite of their excellent activity of these 1-phenyl-3-(1,2,3-thiadiazole-5-yl-)-ureas heretofore applied as cotton defoliants, there has existed and still exists a need for improved agents for this purpose.

The object of the instant invention is therefore to make available new 1,2,3-thiadiazole-5-yl-urea derivatives, structural analogs of which are known to the art as cotton deleafing or defoliating agents which especially in their defoliating activity will surpass the heretofore known compounds.

This object is realized in accordance with the invention by new 1,2,3-thiadiazole-5-yl-urea derivatives having the formula

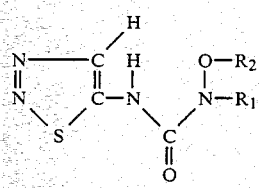

I in which $R_1$ is an aromatic hydrocarbon group which may be substituted with one or more members of the group consisting of $C_1$–$C_6$-alkyl, halogen, $C_1$–$C_6$-alkoxy, nitro and trifluoromethyl and $R_2$ is hydrogen, a monovalent metal or its metal equivalent, a substituted or unsubstituted $C_1$–$C_6$-alkyl, a $C_3$–$C_6$alkenyl or alkinyl, a substituted or unsubstituted aryl-$C_1$–$C_2$-alkyl or the group

wherein $R_3$ is hydrogen, a substituted or unsubstituted $C_1$–$C_{10}$-alkyl, $C_2$–$C_6$-alkenyl, $C_2$–$C_6$-alkinyl, an aryl-$C_1$–$C_2$-alkyl, a $C_3$–$C_8$-aliphatic hydrocarbon group which may be substituted with one or more $C_1$–$C_6$-alkyl substituents, an aromatic hydrocarbon group which may be substituted with at least one of $C_1$–$C_6$-alkyl, halogen, $C_1$–$C_6$-alkoxy, nitro and trifluoromethyl, a substituted or unsubstituted heterocyclic hydrocarbon, $C_1$–$C_6$-alkoxy, $C_3$–$C_6$-alkenyl-, or alkinyloxy, a substituted or unsubstituted aryloxy, a $C_1$–$C_4$-alkylthio or arylthio or an amino group

wherein $R_4$ and $R_5$ are each the same or different and are selected from the group consisting of hydrogen, $C_1$–$C_6$-alkyl, aryl or aryl substituted with one or more members selected from the group consisting of $C_1$–$C_6$-alkyl, halogen, $C_1$–$C_6$-alkoxy, nitro and trifluoromethyl.

The compounds of the invention are suitable for defoliating cotton plants and surprisingly they surpass in this regard the known agents of analogous structure as well also the other defoliating agents known heretofore. The requirement for material, equipment and personnel for preparation and for harvesting the crops are considerably less burdensome when using the compounds of the invention. Further the application of the compounds of the invention enhance the value of the agricultural crops, hasten the maturity thereof and permit optimum harvest to be obtained.

The compounds in accordance in the invention delay the vegetative growth. Generally the effect which is obtained can be designed as a retardation. It is assumed that an alteration of the hormone activity of the plant is produced, i.e., that the compounds of the invention have a selected hormonal activity directed to the leafy structures of the plant without in the concentrations employed having a herbicidal effect. The regulating of the natural growth is visually recognizable through alteration of the size, i.e., shortening of the axis sections of the plant, the shaping, the color or the structure of the treated plant or any of its parts.

For example the following developmental changes of the plant may be noted in addition to the defoliation of the plant which takes place through the application of the compounds of the invention:

Inhibition of vertical growth
Inhibition of root development
Stimulation of bud expulsion
Intensification of the formation of plant color
Prolongation of the harvest period On normal cotton plants which are not treated with defoliating agents the bolls on the lower branches open first while the bolls on the upper branches continue to open slowly over a period of as long as two months from the time when picking of the lower bolls is desirable. The majority of the leaves remain attached to the plant and cause green stains on the cotton when mechanical cotton pickers are employed. In addition the leaves high on the plant shade the lower bolls from sunlight and air resulting in excessive boll rot. At times, 15% of the cotton crop has been lost because of this boll rot. Without the use of defoliating agents, numerous hand pickings are necessary to prevent boll rot and staining. It is the discovery of this invention that the foliage of cotton plants can be treated with many types of the hereindescribed compounds with the result that the leaves are shed.

The compounds of the invention can be applied onto the plants in many different ways and in fact can be applied onto the different plant parts such as the seeds, roots, stems, leaves, blossoms, and the fruits. They can be applied onto the different plant parts as sprays in the early stage or at the start of sprouting or they can be applied after sprouting. The manner and time of application will depend upon the kind and type of vegetation to be defoliated and the density thereof. In the case of cotton, it has been found advantageous to apply the defoliants usually when the bolls are from thirty-five to forty days old. But this may vary with the season and climate.

Again, depending on the purpose of the application, i.e. the type of growth regulation to be achieved and specifically whether it is desired to achieve a more or less total defoliation, increased formation of stems forming shoots, with or without inhibition of vertical growth, etc. the type of plant involved, the time of treatment, different methods of application of the compounds to effect this end will be selected.

The amount of defoliant to be applied will depend upon the kind of vegetation to be defoliated and the density thereof, as well as the choice in concentration of defoliant compounds. The compounds have been found to be effective when applied to normal cotton stands at rates varying from 0.05 to 5 kg per h acre, but it is to be understood that these figures do not represent either maximum or minimum limits.

Non-limiting examples of the compounds of the invention which are excellently suitable for plant growth regulating activity are those in which in formula I above $R_1$ is an aromatic hydrocarbon group as for example phenyl, 2-chlorophenyl, 3-chlorophenyl, 4-chlorophenyl, 2-methylphenyl, 3-methylphenyl, 4-methylphenyl, 2-fluorophenyl, 2-nitrophenyl or 2-methoxyphenyl and $R_2$ is hydrogen, a monovalent metal equivalent as for instance an alkali metal atom preferably a lithium, sodium or potassium atom or a corresponding equivalent of a bivalent metal such as for example a calcium or magnesium atom, a substituted or unsubstituted $C_1$–$C_6$-alkyl as for example methyl, ethyl, propyl, i-propyl, n-butyl, isobutyl, tert.-butyl, 2,2-dimethyl-1-propyl, n-pentyl, n-hexyl, 2-chloroethyl, 3-chloropropyl, 2-bromopropyl, 3-bromopropyl, or 2-phenoxyethyl, $C_3$–$C_6$-alkenyl or alkinyl as for example 2-propenyl, 2-methyl-2-propenyl, or 2-propinyl, a substituted or unsubstituted aryl-$C_1$–$C_2$-alkyl as for example benzyl, 2-chlorobenzyl, 3-chlorobenzyl, 4-chlorobenzyl, 3,4-dichlorobenzyl or the group

wherein $R_3$ is hydrogen, a substituted or unsubstituted $C_1$–$C_{10}$-alkyl as for example methyl, ethyl, propyl, isopropyl, n-butyl, tert.-butyl, n-heptyl, n-nonyl, n-decyl, chloromethyl, fluoromethyl, 2-chloroethyl, 1-chloroethyl, dichloromethyl, phenoxymethyl, 1-phenoxyethyl, 2-phenoxyethyl, (2,4-dichlorophenoxy)-methyl, $C_2$–$C_6$-alkenyl and $C_2$–$C_6$-alkinyl, as for example 2-butenyl, vinyl, 2-methyl-2-propenyl, propen-1-yl, ethinyl, aromatic aliphatic hydrocarbon groups as for example benzyl, 4-chlorobenzyl, $C_3$–$C_8$-cycloaliphatic hydrocarbon groups as for example cyclopropyl, cyclopentyl, cyclohexyl or methylcyclohexyl, aromatic hydrocarbon groups as for example phenyl, 3-chlorophenyl, 2-chlorophenyl, 4-chlorophenyl, 2,4-dichlorophenyl, 2-methylphenyl, 3-methylphenyl, 4-methylphenyl, 3-nitrophenyl, 4-nitrophenyl, 2-methoxyphenyl, 4-methoxyphenyl, 1-naphthyl, 2-naphthyl, 2-furyl, $C_1$–$C_6$-alkoxy as for example methoxy, ethoxy, propoxy, isopropoxy, or n-butoxy, $C_3$–$C_6$-alkenyl-or alkinyl as for example 2-propenyloxy, 2-butenyloxy or 2-propinyloxy, aryloxy as for example phenoxy or 4-chlorophenoxy, $C_1$–$C_4$-alkylthio as for example methylthio, ethylthio, or propylthio, arylthio as for example phenylthio or 4-chlorophenylthio or an amino group

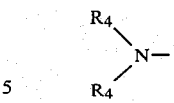

in which $R_4$ and $R_5$ are each the same or different and are selected from the group consisting of hydrogen, methyl, phenyl or 4-chlorophenyl.

The compounds of the invention may be used either alone or in a mixture with one another or with another active substances. Optionally, as a plant protection or pest control agent, such as fungicides, nematocides or other agents may be added according to the desired purpose. The addition of fertilizers may also be desirable or preferable. Examples of such additives include the triazines, aminotriazoles, anilides, diazines, uracils, aliphatic carboxylic acids and halogen carboxylic acids, benzoic acid and aryloxycarboxylic acids, hydrazides, amides, nitriles, esters of such carboxylic acids, carbamic acids and thiocarbamic acid, urea, 2,3,6-trichlorobenzyloxypropanil, thiocyanogen, etc. and other additives as well.

Depending on the purpose of use other substances may also be added for example non-phytotoxic components which can produce with herbicides a synergistic increase of action, such as wetting agents, emulsifiers, solvents, oily additions and the like.

The compounds of the invention can also be admixed with other components as noted above and prefrably with the following examples of plant growth regulating agents and/or defoliants: Auxin
α-(2-Chlorophenoxy)-propionic acid,
4-chlorophenoxyacetic acid,
2,4-dichlorophenoxyacltic acid,
indolyl-3-acetic acid
indolyl-3-butyric acid,
α-naphthylacetic acid,
β-naphthoxyacetic acid,
naphthylacetamide,
N-m-tolylphthalylamidic acid,
gibberelline,
s,s,s-tri-n-butyl-trithiophosphoric acid ester,
cytokinine,
2-chloroethylphosphonic acid,
2-chloro-9-hydroxyfluoro-9-carboxylic acid,
2-chloroethyl-trimethylammoniumchloride,
n,n-dimethylaminosuccinic acid amide,
2-isopropyl-4-trimethylammonio-5-methylphenyl-piperidine-1-carboxylic acid ester chloride,
phenyl-isopropylcarbamate,
3-chlorophenyl-isopropylcarbamate,
ethyl-2-(3-chlorophenylcarbamoyloxy)-propionate,
maleic acid hydrazide,
2,3-dichloroisobutyric acid,
di-(methoxythiocarbonyl)-disulfide,
1,1'-dimethyl-4,4'-bipyridylium-dichloride,
3,6-endoxohexahydrophthalic acid,
3-amino-1,2,4-triazole,
1,2,3-thiadiazolyl-5-yl-urea derivatives,
1-(2-pyridyl)-3-(1,2,3-thiadiazole-5-yl)-urea,
2-butylthio-benzthiazole,
2-(2-methylpropylthio)-benzthiazole,
3,4-dichloroisothiazole-5-carboxylic acid,
2,3-dihydro-5,6-dimethyl-1,4-dithiin-1,1,4,4-tetroxide,
arsenic acid,
cacodylic acid, chlorate, preferably calciumchlorate, potassiumchlorate,
magnesiumchlorate or sodiumchlorate,
claciumcyanamide,
potassiumiodide,
magnesiumchloride,
abietic acid,
nanol.

Appropriately, the active substances according to the invention or their mixtures are used in the form of suitable preparations, such as powders, scatters, granulates, solutions, emulsions or suspensions, with the addition of liquid and/or solid vehicles or diluents and also wetting, adhesive, emulsifying and/or dispersing agents.

Suitable liquid vehicles are water, aliphatic and aromatic hydrocarbons, such as benzene, toluene, xylene, cyclohexanone, isophorone, dimethylformamide, and mineral oil fractions.

As solid vehicles, there are mineral earth, such as siliceous clay, silica gel, talc, kaolin, atta clay, limestone, silicic acid and plant products such as flours.

Among the surface active substances that may be used, there may be mentioned, calcium-lignin sulfonate, polyoxyethyleneoctylphenolether, naphthalene-sulfonic acid and their salts, phenosulfonic acids and their salts, formaldehyde condensates, fatty alcohol sulfates and substituted benzene sulfonic acids and their salts.

The proportion of the active substance or substances in the various preparations may vary within wide limits. The agents contain for example about 5 to 95% by weight of active substances, about 95 to 5% by weight of liquid or solid vehicles as well as possibly up to 20% by weight of surface active substances.

The application of the agents may be effected in the usual manner, such as with water as vehicle in liquid spray quantitites of 100 to 5000 liters/ha. An application of the agents in the so-called "ultra low volume process" is likewise possible as is their application in the form of so-called microgranulates.

For preparing the plant growth regulating compositions for example the following formulation can be made:

A. Spray Powder (a)
80 weight % active agent
15 weight % kaolin
5 weight % surface active agent on the basis of the sodium salts of n-methyl-n-oleyltaurine and the calcium salts of ligninsulfonic acid.

(b)
50 weight % active agent
40 weight % mineral clay
5 weight % cellulose pitch
5 weight % of a surface active agent on the basis of a mixture of the calcium salts of ligninsulfonic acid with alkylphenolpolyglycolethers (c)
20 weight % active agent
70 weight % mineral clay
5 weight % cellulose pitch
5 weight % surface active agent on the basis of a mixture of the calcium salt of ligninsulfonic acid with alkylphenylpolyglycolethers (d)
5 weight % active agent
80 weight % tonsil
10 weight % cellulose pitch
5 weight % surface active agent on the basis of a fatty acid condensation product B. Emulsion Concentrate 20 weight % active agent
40 weight % xylene
35 weight % dimethylsulfoxide
5 weight % of a mixture of nonylphenylpolyoxyethylenes or calciumdodecylbenzenesulfonate.

The new compounds of the invention may be produced by the following methods including the reaction of (A) metal compounds of the formula

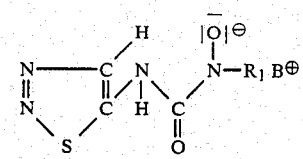

with an acylhalogenide of the formula

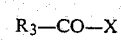

$R_3$—CO—X      III or with an isocyanate of the formula $R_4$—N=C=O      IV or with an alkylhalogenide of the formula $R_2$—X      V or by reacting a (B) 1-hydroxy-3-(1,2,3-thiadiazole-5-yl)-urea of the formula

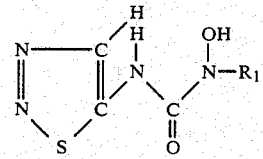

in the presence of an acid binding agent with an acylhalogenide of the formula $R_3$—CO—X      III or with an isocyanate of the formula $R_4$—N=C=O      IV preferably in the presence of a catalyst or with an alkylhalogenide of the formula $R_2$—X      V or by reacting (C) 1-hydroxy-3-(1,2,3-thiadiazole-5-yl)-urea of the formula

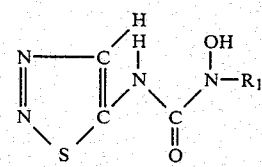

with an acid anhydride of the formula

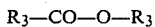    VII preferably in the presence of a catalyst, wherein $R_1$, $R_2$, $R_3$, and $R_4$ all have the above indicated meanings, X is halogen preferably a chlorine atom and B is a univalent metal or its equivalent, preferably a sodium, potassium or lithium atom, or in the case that $R_2$ is hydrogen, then the following are reacted (D) 5-amino-1,2,3-thiadiazole of the formula

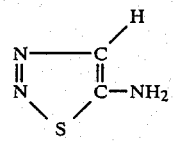    VIII with (a) a chloroformic acid ester of the formula

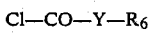

in the presence of an acid binding agent as for example triethylamine, N,N-dimethylaniline, hexamethylphosphoricacidtriamide or a pyridine base, in an organic solvent as for example tetrahydrofuran, methylenechloride or dimethylformamide, at a temperature of from 0° C. to 60° C. and preferably at room temperature, and then reacting the reaction product with an hydroxyl amine derivative of the formula

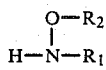    IX dissolved in an organic solvent as for example acetone, dimethylformamide, tetrahydrofuran or acetonitrile at a temperature of between 50° and 150° C., preferably at the boiling temperature of the solvent or (b) first reacting the 5-amino-1,2,3-thiadiazole of formula VIII above with phosgene in the presence of an acid binding agent as for example N,N-dimethylaniline under formation of a corresponding isocyanate or carbamoyl chloride and then reacting the reaction product with an hydroxyl amine derivative of the formula

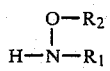    IX or (E) reacting a 1,2,3-thiadiazole-5-carboxylic acid amide of the formula

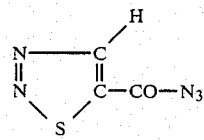    X with a hydroxylamine derivative of the formula

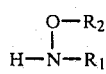    IX in an inert organic solvent as for example toluene, xylene, benzene, dioxan or cyclohexanone at a temperature of from 20° to 180° C., preferably at the boiling temperature of the reaction mixture or (F) by reacting a 1,2,3-thiadiazole-5-carbohydroxamic acid of the formula

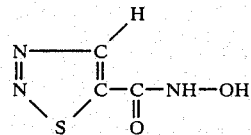    XI with an acid halogenide of the formula $R_7$—X    XII and a hydroxylamine derivative of the formula

    IX in an inert organic solvent as for example tetrahydrofuran, acetonitrile or toluene, in the presence of an acid binding agent as for example triethylamine, pyridine or sodium carbonate whereby $R_1$ and $R_2$ have the above-indicated meaning, X is a halogen atom preferably a chlorine atom, Y is oxygen or sulfur, $R_6$ is a $C_1$-$C_5$-alkyl for example methyl or ethyl or an aryl group as for example phenyl and $R_7$ is a substituted or unsubstituted aryl or as the case may be alkylsulfonoyl group for example phenylsulfonyl, 4-tolylsulfonyl, 4-bromophenylsulfonyl, 4-chlorophenylsulfonyl, 4-nitrophenylsulfonyl, methylsulfonyl, ethylsulfonyl or benzylsulfonyl or if $R_2$ is a univalent metal, then reacting (G) 1-hydroxy-3-(1,2,3-thiadiazole-5-yl)-urea having the formula

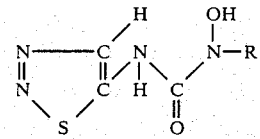    VI with a metal compound of the formula

BZ    XIII preferably in the presence of a solvent as for example acetonitrile, tetrahydrofuran, dioxan, methanol or dimethylformamide, whereby $R_1$ and B have the above-indicated meanings and Z is hydrogen, hydroxyl, lower alkoxy or amino.

The starting materials used in the process of the invention are known compounds and can be prepared by the known methods.

The reaction of the reaction components takes place at a temperature of between 0° and 120° C. and most preferably at a temperature between room temperature and the reflux temperature of the corresponding reaction mixtures.

The duration of the reaction usually amounts to from 1 to 72 hours.

In synthesizing the compounds of the invention, the reactants are charged in about equimolar amounts. Suitable reaction media are solvents which are inert to the reactants. The choice of solvent and/or suspension agent depends to some extent on the alkyl- or acylhalogenide, the isocyanate, the acid acceptor and the metal compounds used. As solvents and/or suspension agents the following may be named: ethers such as diethylether, diisopropylether, tetrahydrofuran and dioxan, aliphatic and aromatic hydrocarbons as for example petroleum ether, cyclohexane, hexane, heptane, benzene, toluene, and xylene, carboxylic acid nitriles as for example acetonitrile and carboxylic acid amides as for example dimethylformamide.

As acid acceptors there are suitable such organic bases as for example triethylamine, N,N-dimethylaniline and the pyridine bases or inorganic bases as for example oxides, hydroxides, and carbonates of the alkaline earth and alkali metals. Liquid bases such as for example the pyridines can serve not only as acid acceptors but also as the solvents.

The compounds of the invention can be recovered from the reaction mixtures in the customary manner as for example by distilling off the solvents under normal or reduced pressure or by precipitation by the introduction of water.

The compounds of the invention are generally speaking colorless and odorless crystalline bodies which are difficultly soluble in water and aliphatic hydrocarbons but which are readily soluble in halogenated hydrocarbons such as chloroform and tetrachlorohydrocarbon, ketones such as acetone, carboxylic acid amides such as dimethylformamide, sulfoxides such as dimethylsulfoxide, carboxylic acid nitriles such as acetonitrile and lower alcohol such as methanol and ethanol.

As solvents for crystallization there come into consideration such solvents as tetrachlorohydrocarbon, chloroform, toluene, acetonitrile and acetic acid ester.

The following examples are given to illustrate the preparation of the compounds of the invention. The examples are illustrative only.

EXAMPLE I 1-hydroxy-1-phenyl-3-(1,2,3-thiadiazole-5-yl)-urea

The solution of 7.25 g (0.105 mole) sodium nitrite in 100 ml water and 200 ml toluene are introduced into a triple branch tubulated 1 liter round flask provided with a thermometer and stirrer. Into this mixture within 30 minutes at a temperature of from 0° to 5° C. a solution as follows is introduced in dropwise fashion, 14.4 g (0.1 mole) 1,2,3-thiadiazole-5-carboxylic acid hydrazide, 100 ml water and 8 ml (about 0.1 mole) concentrated hydrochloric acid. The mixture is stirred for about 15 minutes at about 0° to 5° C., thereafter the toluene phase is separated off and dried over magnesium sulfate.

In a triple branched tubulated 1 liter round flask provided with a stirrer thermometer and reflux cooler there is at this time heated to 110° C. 50 ml of toluene. The dried 1,2,3-thiadiazole-5-carboxylic acid azide solution and a solution of 11.0 g (0.11 mole) phenylhydroxylamine in 200 ml toluene are simultaneously but separately within about 15 minutes introduced in dropwise fashion so that the temperature is maintained at from 100° to 110° C. Stirring is continued for a further 10 minutes under reflux whereby even before the end of this period light yellow colored crystals separate out. The reaction mixture is then cooled down to about 5° C., the crystals separated off, digested with about 50 ml diisopropylether and dried in vacuum at about 40° C. until a constant weight is obtained.

Yield: 19.6 g = 82.9% of theory
Fp.: 177° C. (decomposition)
DC: flow agent = acetic acid ester $R_f$-value: 0.445
Analysis: calculated C 45.76%; H 3.41%; N 23.72%; S 13.54%; found C 45.67%; H 3.29%; N 23.54%; S 13.19%.

EXAMPLE II 1-phenyl-1-propionyloxy-3-(1,2,3-thiadiazole-5-yl)-urea 9.43 g (0.04 mole) 1-hydroxy-1-phenyl-3-(1,2,3-thiadiazole-5-yl)-urea were under addition of 6.15 ml (0.044 mole) triethylamine dissolved in 100 ml tetrahydrofuran. There were added to this solution under cooling to 20° C., a solution of 3.46 ml (0.04 mole) propionylchloride in 10 ml tetrahydrofuran within about 5 minutes in dropwise fashion and thereafter the resulting mixture was stirred for an hour. After separating off the precipitate which had formed the filtrate was concentrated and the residue taken up in 150 ml of ether. The ether phase was washed with water, dried over magnesium sulfate, again concentrated and the residue digested with diisopropylether.

Yield: 8.2 g = 70.1% of theory
Fp.: 115° C. (decomposition)
DC: flow agent = acetic acid ester $R_f$-value: 0.475
Analysis: calculated C 49.30%; H 4.14%; N 19.17%; found C 49.42%; H 4.23%; N 19.19%.

EXAMPLE III 1-methylcarbamoyloxy-1-phenyl-3-(1,2,3-thiadiazole-5-yl)-urea 4.72 g (0.02 mole) 1-hydroxy-1-phenyl-3-(1,2,3-thiadiazole-5-yl)-urea were suspended in 40 ml tetrahydrafuran and then reacted with 1.19 ml (0.02 mole) methylisocyanate. After addition of 3 drops of triethylamine there is obtained a clear solution and after a further 10 minutes crystals already begin to separate out. The reaction mixture is allowed to stand at room temperature. Thereafter the crystals are separated off and digested with diisopropylether.

Yield: 4.7 g = 80.1% of theory
Fp.: 135° C. (decomposition)
DC: flow agent = acetic acid ester $R_f$-value: 0.290
Analysis: calculated: C 45.04%; H 3.78%; N 23.88%; found: C 45.57%; H 3.77%; N 24.29%.

EXAMPLE IV 1-methoxy-1-phenyl-3-(1,2,3-thiadiazole-5-yl)-urea 7.1 g (0.03 mole) 1-hydroxy-1-phenyl-3-(1,2,3-thiadiazole-5-yl)-urea were dissolved in 75 ml tetrahydrafuran and reacted with 1.44 g (0.03 mole) of a 50% dispersion of sodium hydride in oil. After an hour had elapsed at room temperature all of the gas evolvement had been completed and then 1.9 ml (0.03 mole) methyliodide were introduced and the reaction mixture over a period of 30 minutes heated to 60° C. Thereafter the reaction mixture was concentrated in vacuum and reacted with 100 ml of ice water. The resulting greasy crystals were digested with 50 ml diisopropylether and dried to a constant weight at 40° C. in vacuum.

Yield: 3.8 g = 50.7% of theory
Fp.: 163°–164° C. (decomposition)
DC: flow agent = acetic acid ester $R_f$-value: 0.45
Analysis: calculated: C 47.99%; H 4.04%; N 22.39%; found: C 47.80%; H 4.03%; N 21.98%.

The following compounds were prepared by analogous reaction:

| Compound Name | Physical Constant |
|---|---|
| 1-acetoxy-1-phenyl-3-(1,2,3-thiadiazole-5-yl)-urea | Fp.: 155° C. (decomposition) |
| 1-ethoxy-1-phenyl-3-(1,2,3-thiadiazole-5-yl)-urea | Fp.: 167–168° C. |
| 1-phenyl-1-phenylcarbamoyloxy-3-(1,2,3-thiadiazole-5-yl)-urea | Fp.: 115° C. (decomposition) |
| 1-chloroacetoxy-1-phenyl-3-(1,2,3-thiadiazole-5-yl)-urea | Fp.: 70° C. (decomposition) |
| 1-benzyloxy-1-phenyl-3-(1,2,3-thiadiazole-5-yl)-urea | Fp.: 130° C. (decomposition) |
| 1-isobutyryloxy-1-phenyl-3-(1,2,3-thiadiazole-5-yl)-urea | Fp.: 85° C. (decomposition) |
| 1-butyryloxy-1-phenyl-3-(1,2,3-thiadiazole-5-yl)-urea | Fp.: 127° C. (decomposition) |
| 1-benzoyloxy-1-phenyl-3-(1,2,3-thiadiazole-5-yl)-urea | Fp.: 165° C. (decomposition) |
| 1-(2-chlorobenzoyloxy)-1-phenyl-3-(1,2,3-thiadiazole-5-yl)-urea | Fp.: 113° C. (decomposition) |
| 1-dimethylcarbamoyloxy-1-phenyl-3-(1,2,3-thiadiazole-5-yl)-urea | Fp.: 102° C. (decomposition) |
| 1-phenyl-1-propoxy-3-(1,2,3-thiadiazole-5-yl)-urea | Fp.: 134–136° C. (decomposition) |
| 1-cyclopropylcarbonyl-3-phenyl-1-(1,2,3-thiadiazole-5-yl)-urea | Fp.: 139° C. |
| 1-(2,2-dimethylpropionyl)-3-phenyl-1-(1,2,3-thiadiazole-5-yl)-urea | Fp.: 245° C. (decomposition) |
| 1-decylcarbonyl-3-phenyl-1-(1,2,3-thiadiazole-5-yl)-urea | $n_D^{20}$: 1.5401 |
| 1-cyclohexylcarbonyl-3-phenyl-1-(1,2,3-thiadiazole-5-yl)-urea | Fp.: 135–136° C. |
| 1-formyl-3-phenyl-1-(1,2,3-thiadiazole-5-yl)-urea | Fp.: 155–157° C. (decomposition) |

The following examples illustrate the plant growth regulating effect for the compounds of the invention as well as their possibilities of use.

EXAMPLE V

In a greenhouse test the following plants Sinapis (Si), Solanum (So), Beta (Be), Gossypium (Go), Hordeum (Ho), Zea Mays (Ze), Lolium (Lo) and Setaria (Se) before and following emergence were treated with a quantity of 5 kg active agent/ha dispersed in 600 liters of water of the compounds of the invention listed in the table below. The active substances were formulated as a spray. The growth regulating effects were determined three weeks after the treatment. The measured results were set in relation to the effect before (V) and after the following spray treatment (N) whereby 0 = no activity
1–2 = growth regulating effect in the form of intensive coloration of the primary leaves
retardation
growth decreased and a decrease in the size of the leaves decreased root development
3–4 = the effects described under 1 and 2 but to a greater degree.

| Compound (Invention) | Si V/N | So V/N | Be V/N | Go V/N | Ho V/N | Ze V/N | Lo V/N | Se V/N |
|---|---|---|---|---|---|---|---|---|
| 1-hydroxy-1-phenyl-3-(1,2,3-thiadiazole-5-yl)-urea | 4/3 | 4/3 | 4/4 | 3/4 | 1/1 | 2/1 | 3/3 | 3/4 |
| 1-acetoxy-1-phenyl-3-(1,2,3-thiadiazole-5-yl)-urea | 2/3 | 3/2 | 3/3 | 3/4 | 2/1 | 2/2 | 3/3 | 3/4 |
| 1-methoxy-1-phenyl-3-(1,2,3-thiadiazole-5-yl)-urea | 4/3 | 4/2 | 2/3 | 2/3 | 0/0 | 1/0 | 3/1 | 3/3 |
| 1-ethoxy-1-phenyl-3-(1,2,3-thiadiazole-5-yl)-urea | 0/3 | 0/1 | 1/3 | 0/3 | 0/0 | 0/0 | 2/0 | 1/3 |
| 1-methylcarbamoyloxy-1-phenyl-3-(1,2,3-thiadiazole-5-yl)-urea | 3/2 | 1/2 | 3/3 | 2/3 | 2/1 | 2/1 | 2/2 | 3/4 |
| 1-phenyl-1-phenylcarbamoyloxy-3-(1,2,3-thiadiazole-5-yl)-urea | 1/3 | 1/3 | 3/3 | 3/4 | 1/0 | 1/0 | 3/3 | 3/3 |
| 1-chloroacetoxy-1-phenyl-3-(1,2,3-thiadiazole-5-yl)-urea | 1/3 | 1/3 | 3/3 | 2/4 | 1/1 | 1/1 | 3/1 | 2/3 |
| 1-phenyl-1-propionyloxy-3-(1,2,3-thiadiazole-5-yl)-urea | 3/3 | 3/3 | 4/3 | 3/4 | 2/1 | 1/2 | 3/3 | 3/3 |
| 1-benzyloxy-1-phenyl-3-(1,2,3-thiadiazole-5-yl)-urea | 0/2 | 0/2 | 0/3 | 0/3 | 0/1 | 1/0 | 1/1 | 1/3 |
| 1-isobutyryloxy-1-phenyl-3-(1,2,3-thiadiazole-5-yl)-urea | 3/3 | 3/3 | 3/3 | 3/4 | 3/2 | 2/2 | 3/3 | 3/4 |
| 1-butyryloxy-1-phenyl-3-(1,2,3-thiadiazole-5-yl)-urea | 3/3 | 3/3 | 2/3 | 2/3 | 1/3 | 1/1 | 3/2 | 2/4 |
| 1-benzoyloxy-1-phenyl-3-(1,2,3-thiadiazole-5-yl)-urea | 3/3 | 3/3 | 3/3 | 3/3 | 1/1 | 1/1 | 3/2 | 2/3 |
| 1-(2-chlorobenzoyloxy)-1-phenyl-3-(1,2,3-thiadiazole-5-yl)-urea | 3/3 | 3/3 | 3/3 | 3/3 | 1/1 | 1/1 | 3/2 | 2/1 |
| 1-dimethylcarbamoyloxy-1-phenyl-3-(1,2,3-thiadiazole-5-yl)-urea | 3/3 | 3/3 | 3/3 | 3/3 | 1/1 | 1/1 | 3/3 | 2/3 |
| 1-phenyl-1-propoxy-3-(1,2,3-thiadiazole-5-yl)-urea | 3/4 | 3/4 | 4/4 | 2/3 | 0/0 | 2/1 | 3/2 | 2/3 |

EXAMPLE VI

In a greenhouse test, the plant species listed in the table below were treated before emergence with quantities of active agent amounting to 3 kg/ha of the named compounds of the invention. The active substances were applied in 500 liters of water/ha. The application was made directly onto the soil. Three weeks after treatment the effects were appraised according to the following appraisal scheme.

0–10, whereby
0–3 = strong
4–7 = average and
8–10 = no growth inhibition

Depending on the plant type and the active substance used the inhibition effect varied in degree and usefulness.

| 3 kg active agent/ha | 1-hydroxy-1-phenyl-3-(1,2,3-thiazole-5-yl)-urea | 1-acetoxy-1-phenyl-3-(1,2,3-thiadiazole-5-yl)-urea | 1-ethoxy-1-phenyl-3-(1,2,3-thiadiazole-5-yl)-urea | 1-methoxy-1-phenyl-3-(1,2,3-thiadiazole-5-yl)-urea | 1-butyryloxy-1-phenyl-3-(1,2,3-thiadiazole-5-yl)-urea | 1-benzoyloxy-1-phenyl-3-(1,2,3-thiadiazole-5-yl)-urea |
|---|---|---|---|---|---|---|
| Brassica | 1 | 0 | 1 | 1 | 0 | 1 |
| Solanum | 1 | 2 | 2 | 1 | 5 | 4 |
| Allium | 3 | 3 | 2 | 3 | 3 | 8 |
| Cucumis | 1 | 0 | 2 | 0 | 0 | 0 |
| Medicago | 2 | 1 | 0 | 2 | 4 | 2 |
| Phaseolus | 5 | 3 | 2 | 2 | 9 | 8 |
| Helianthus | 2 | 0 | 5 | 2 | 0 | 5 |
| Stellaria media | 1 | 0 | 3 | 1 | 1 | 2 |
| Abutilon theophrastii | 0 | 0 | 1 | 0 | 0 | 1 |
| Matricaria chamomilla | 1 | 0 | 0 | 0 | 0 | 0 |
| Viola tricolor | 1 | 0 | 0 | 0 | 0 | 1 |
| Centaurea cyanus | 5 | 0 | 0 | 1 | 2 | 3 |
| Amaranthus retroflexus | 0 | 1 | 2 | 0 | 0 | 1 |
| Galium asparine | 2 | 5 | 0 | 0 | — | — |
| Chrysanthemum segetum | 1 | 0 | 1 | 1 | 0 | 0 |
| Ipomea purpurea | 2 | 10 | 6 | 6 | 7 | 9 |
| Fagopyrum esculentum | 5 | 10 | 7 | 3 | — | — |
| Avena fatua | 3 | 3 | 4 | 3 | 3 | 5 |
| Alopecurus myosuroides | 3 | 4 | 6 | 3 | 1 | 5 |
| Echinochloa crus galli | 1 | 3 | 2 | 2 | 0 | 2 |
| Setaria italica | 4 | 3 | 4 | 3 | 3 | 6 |
| Digitaria sanguinalis | 1 | 1 | 3 | 3 | 1 | 1 |
| Cyperus esculentus | 6 | 10 | 5 | 4 | 7 | 9 |
| Sorghum halepense | 1 | 5 | 3 | 6 | 3 | 5 |
| Poa annua | 3 | 1 | 2 | 2 | 2 | 3 |
| Untreated | 10 | 10 | 10 | 10 | 10 | 10 |

| 3 kg/ha active agent | 1-benzoyloxy-1-phenyl-3-(1,2,3-thiadiazole-5-yl)-urea | 1-(2-chlorobenzoyloxy)-1-phenyl-3-(1,2,3-thiadiazole-5-yl)-urea | 1-dimethylcarbamoyloxy-1-phenyl-3-(1,2,3-thiadiazole-5-yl)urea | 1-phenyl-1-propoxy-3-(1,2,3-thiadiazole-5-yl)-urea | 1-isobutyryl-1-phenyl-3-(1,2,3-thiadiazole-5-yl)-urea |
|---|---|---|---|---|---|
| Brassica | 1 | 1 | 1 | 0 | 0 |
| Solanum | 4 | 9 | 5 | 5 | 1 |
| Allium | 8 | 6 | 5 | 3 | 3 |
| Cucumis | 0 | 1 | 0 | 0 | 0 |
| Medicago | 2 | 9 | 5 | 0 | 1 |
| Phaseolus | 8 | 10 | 10 | 10 | 4 |
| Helianthus | 5 | 8 | 2 | 7 | 0 |
| Stellaria media | 2 | 0 | 0 | 0 | 0 |
| Abutilon theophrastii | 1 | 6 | 1 | 1 | 0 |
| Matricaria chamomilla | 0 | 0 | 0 | 0 | 0 |
| Viola tricolor | 1 | 1 | 1 | 0 | 0 |
| Centaurea cyanus | 3 | 7 | 1 | 1 | 0 |
| Amaranthus retroflexus | 1 | 0 | 1 | 0 | 0 |
| Galium aparine | — | — | — | — | — |
| Chrysanthemum segetum | 0 | 0 | 0 | 0 | 0 |
| Ipomea purpurea | 9 | 10 | 10 | 10 | 8 |
| Fagopyrum esculentum | — | — | — | — | — |
| Avena fatua | 5 | 10 | 5 | 8 | 2 |
| Alopecurus myosuroides | 5 | 8 | 7 | 8 | 3 |
| Echinochloa crus galli | 5 | 5 | 5 | 3 | 0 |
| Setaria italica | 6 | 6 | 7 | 5 | 2 |
| Digitaria sanguinalis | 1 | 1 | 1 | 1 | 1 |
| Cyperus esculentus | 9 | 10 | 10 | 10 | 10 |
| Sorghum halepense | 5 | 10 | 6 | 8 | 2 |
| Poa annua | 3 | 8 | 5 | 7 | 1 |
| Untreated | 10 | 10 | 10 | 10 | 10 |

-continued

| 3 kg active agent/ha | 1-phenyl-1-phenylcarbamoyl-oxy-3-(1,2,3-thiadiazole-5-yl)-urea | 1-chloroacetoxy-1-phenyl-3-(1,2,3-thiadiazole-5-yl)-urea | 1-phenyl-propion-yloxy-3-(1,2,3-thiadiazole-5-yl)-urea | 1-methylcarbam-oyloxy-1-phenyl-3-(1,2,3-thiadia-zole-5-yl)-urea |
|---|---|---|---|---|
| Brassica | 0 | 0 | 1 | 1 |
| Solanum | 1 | 3 | 1 | 2 |
| Allium | 1 | 10 | 3 | 3 |
| Cucumis | 0 | 1 | 0 | 0 |
| Medicago | 3 | 8 | 3 | 3 |
| Phaseolus | 3 | 3 | 5 | 5 |
| Helianthus | 0 | 3 | 0 | 0 |
| Stellaria media | 0 | 0 | 1 | 1 |
| Abutilon theophrastii | 0 | 0 | 0 | 0 |
| Matricaria chamomilla | 0 | 0 | 0 | 0 |
| Viola tricolor | 0 | 0 | 0 | 0 |
| Centaurea cyanus | 0 | 2 | 0 | 1 |
| Amaranthus retroflexus | 0 | 0 | 0 | 0 |
| Galium aparine | — | — | — | — |
| Chrysanthemum segetum | 0 | 0 | 0 | 0 |
| Ipomea purpurea | 8 | 8 | 4 | 5 |
| Fagopyrum esculentum | — | — | 4 | 3 |
| Avena fatua | 2 | 5 | 3 | 4 |
| Alopecurus myosuroides | 1 | 3 | 2 | 2 |
| Echinochloa crus galli | 0 | 1 | 1 | 1 |
| Setaria italica | 1 | 5 | 1 | 3 |
| Digitaria sanguinalis | 0 | 2 | 1 | 1 |
| Cyperus esculentus | 8 | 10 | 10 | 10 |
| Sorghum halepense | 3 | 10 | 4 | 3 |
| Poa annua | 1 | 2 | 1 | 1 |
| Untreated | 10 | 10 | 10 | 10 |

EXAMPLE VII

In a greenhouse test the hereinafter named compounds of the invention were applied onto the plants after emergence thereof in an amount of 1 kg or 3 kg active agent. The agent was for this purpose used in 500 liters of water/ha and in this form applied onto the test plant. 14 Days after this treatment the results were evaluated according to the following evaluation scheme:

0–3 = strong growth inhibition
4–7 = average growth inhibition
8–10 = no growth inhibition.

The results show that the compounds in accordance with the invention inhibit the growth of a large number of the plants to various degrees.

| Kg active agent/ha | 1-hydroxy-1-phenyl-3-(1,2,3-thiadiazole-5-yl)-urea<br>1 | 1-acetoxy-1-phenyl-3-(1,2,3-thiadiazole-5-yl)-urea<br>1 | 1-methoxy-1-phenyl-3-(1,2,3-thiadiazole-5-yl)-urea<br>3 | 1-ethoxy-1-phenyl-3-(1,2,3-thiadiazole-5-yl)-urea<br>3 | 1-phenyl-1-phenyl-carbamoyloxy-3-(1,2,3-thiadiazole-5-yl)-urea<br>3 |
|---|---|---|---|---|---|
| Allium | 10 | 9 | 6 | 7 | 8 |
| Cucumis | 0 | 0 | 0 | 0 | 0 |
| Medicago | 3 | 5 | 3 | 2 | 4 |
| Phaseolus | 5 | 5 | 2 | 4 | 2 |
| Glycine | 10 | 10 | 8 | 7 | 9 |
| Helianthus | 4 | 1 | 2 | 2 | 4 |
| Stellaria media | 4 | 3 | 3 | 4 | 3 |
| Abutilon | 1 | 0 | 0 | 0 | 2 |
| Matricaria chamomilla | 10 | 2 | 4 | 4 | 0 |
| Viola tr. | 10 | 4 | 2 | 3 | 2 |
| Centaurea cyanus | 8 | 5 | 1 | 4 | 4 |
| Amaranthus retroflexus | 0 | 0 | 0 | 0 | 0 |
| Galium aparine | 10 | 10 | 6 | 3 | 8 |

| Kg active agent/ha | 1-chloroacetoxy-1-phenyl-3-(1,2,3-thiadiazole-5-yl)-urea<br>3 | 1-phenyl-1-propion-yloxy-3-(1,2,3-thiadiazole-5-yl)-urea<br>3 | 1-butyryloxy-phenyl-3-(1,2,3-thiadiazole-5-yl)-urea<br>3 | 1-benzoyloxy-1-phenyl-3-(1,2,3-thiadiazole-5-yl)-urea<br>3 | 1-(2-chlorobenzoyl-oxy)-1-phenyl-3-(1,2,3-thiadiazole-5-yl)-urea<br>3 |
|---|---|---|---|---|---|
| Allium | 7 | 8 | 7 | 7 | 7 |
| Cucumis | 2 | 0 | 0 | 0 | 0 |

-continued

| | | | | | |
|---|---|---|---|---|---|
| Medicago | 6 | 6 | 4 | 3 | 4 |
| Phaseolus | 4 | 5 | 3 | 3 | 4 |
| Glycine | 9 | 9 | 6 | 8 | 8 |
| Helianthus | 4 | 2 | 1 | 1 | 3 |
| Stellaria media | 6 | 4 | 4 | 5 | 4 |
| Abutilon | 2 | 0 | 0 | 0 | 3 |
| Matricaria chamomilla | 2 | 1 | 4 | 4 | 6 |
| Viola tr. | 2 | 2 | 4 | 2 | 3 |
| Centaurea cyanus | 4 | 3 | 3 | 5 | 2 |
| Amaranthus retroflexus | 3 | 0 | 1 | 0 | 5 |
| Galium aparine | 9 | 9 | 7 | 6 | 7 |

| Kg active agent/ha | 1-dimethylcarba-moyloxy-1-phenyl-3-(1,2,3-thiadiazole-5-yl)-urea 3 | 1-methylcarbamoyl-oxy-1-phenyl-3-(1,2,3-thiadiazole-5-yl)-urea 3 | 1-benzyloxy-1-phenyl-3-(1,2,3-thiadiazole-5-yl)-urea 3 | 1-isobutyryloxy-1-phenyl-3-(1,2,3-thiadiazole-5-yl)-urea 3 | 1-phenyl-1-propoxy-3-(1,2,3-thiadiazole-5-yl)-urea 3 |
|---|---|---|---|---|---|
| Allium | 7 | 7 | 8 | 8 | 2 |
| Cucumis | 0 | 0 | 0 | 1 | 1 |
| Medicago | 6 | 5 | 7 | 5 | 1 |
| Phaseolus | 4 | 4 | 5 | 3 | 4 |
| Glycine | 8 | 10 | 10 | 10 | 7 |
| Helianthus | 3 | 3 | 3 | 3 | 2 |
| Stellaria media | 4 | 2 | 5 | 4 | 0 |
| Abutilon | 0 | 0 | 1 | 0 | 0 |
| Matricaria chamomilla | 6 | 2 | 3 | 2 | 4 |
| Viola tr. | 2 | 0 | 3 | 0 | 0 |
| Centaurea cyanus | 6 | 3 | 6 | 4 | 0 |
| Amaranthus retroflexus | 2 | 0 | 2 | 0 | 0 |
| Galium aparine | 7 | 10 | 9 | 8 | 10 |

| Kg active agent/ha | 1-hydroxy-1-phenyl-3-(1,2,3-thiadiazole-5-yl)-urea 3 | 1-acetoxy-1-phenyl-3-(1,2,3-thiadiazole-5-yl)-urea 3 | 1-methoxy-1-phenyl-3-(1,2,3-thiadiazole-5-yl)-urea 3 | 1-ethoxy-1-phenyl-3-(1,2,3-thiadiazole-5-yl)-urea 3 | 1-phenyl-1-phenyl-carbamoyloxy-3-(1,2,3-thiadiazole-5-yl)-urea 3 |
|---|---|---|---|---|---|
| Chrysanthemum segetum | 5 | 2 | 2 | 1 | 4 |
| Ipomea purpurea | 10 | 10 | 6 | 6 | 5 |
| Fagopyrum es. | — | 8 | 3 | 4 | 8 |
| Avena | 10 | 9 | 7 | 6 | 6 |
| Alopecurus | 10 | 10 | 8 | 7 | 8 |
| Echinochloa crus gall galli | 10 | 9 | 7 | 6 | 8 |
| Setaria italica | 4 | 4 | 3 | 3 | 4 |
| Digitaria sanguinalis | 8 | 9 | 7 | 7 | 7 |
| Cyperus es. | 10 | 10 | 8 | 5 | 7 |
| Sorghum halepense | 10 | 9 | 7 | 6 | 6 |
| Poa annua | 10 | 5 | 7 | 6 | 4 |
| Untreated | 10 | 10 | 10 | 10 | 10 |

| Kg active agent/ha | 1-chloroacetoxy-1-phenyl-3-(1,2,3-thiadiazole-5-yl)-urea 3 | 1-phenyl-1-propion-yloxy-3-(1,2,3-thiadiazole-5-yl)-urea 3 | 1-butyryloxy-phenyl-3-(1,2,3-thiadiazole-5-yl)-urea 3 | 1-benzoyloxy-1-phenyl-3-(1,2,3-thiadiazole-5-yl)-urea 3 | 1-(2-chlorobenzoyl-oxy)-1-phenyl-3-(1,2,3-thiadiazole-5-yl)-urea 3 |
|---|---|---|---|---|---|
| Chrysanthemum segetum | 5 | 3 | 3 | 2 | 6 |
| Ipomea purpurea | 6 | 5 | 6 | 6 | 7 |
| Fagopyrum es. | 9 | 4 | 2 | 3 | 4 |
| Avena | 5 | 5 | 6 | 3 | 7 |
| Alopecurus | 9 | 5 | 7 | 7 | 8 |
| Echinochloa crus gall galli | 7 | 4 | 6 | 6 | 7 |
| Setaria italica | 3 | 0 | 2 | 6 | 6 |
| Digitaria sanguinalis | 9 | 7 | 3 | 6 | 8 |
| Cyperus es. | 9 | 7 | 5 | 6 | 9 |
| Sorghum halepense | 6 | 9 | 6 | 6 | 9 |
| Poa annua | 8 | 3 | 8 | 8 | 9 |
| Untreated | 10 | 10 | 10 | 10 | 10 |

| Kg active agent/ha | 1-dimethylcarba-moyloxy-1-phenyl-3-(1,2,3-thiadiazole-5-yl)-urea 3 | 1-methylcarbamoyl-oxy-1-phenyl-3-(1,2,3-thiadiazole-5-yl)-urea 3 | 1-benzyloxy-1-phenyl-3-(1,2,3-thiadiazole-5-yl)-urea 3 | 1-isobutyryloxy-1-phenyl-3-(1,2,3-thiadiazole-5-yl)-urea 3 | 1-phenyl-1-propoxy-3-(1,2,3-thiadiazole-5-yl)-urea 3 |
|---|---|---|---|---|---|
| Chrysanthemum segetum | 5 | 3 | 3 | 4 | 1 |
| Ipomoea purpurea | 7 | 4 | 5 | 5 | 0 |
| Fagopyrum es. | 3 | 3 | 8 | 4 | 0 |
| Avena | 7 | 6 | 6 | 7 | 9 |
| Alopecurus | 8 | 6 | 6 | 7 | 9 |
| Echinochloa crus galli | 7 | 8 | 9 | 5 | 7 |
| Setaria italica | 3 | 2 | 4 | 0 | 4 |
| Digitaria sanguinalis | 4 | 6 | 7 | 7 | 5 |
| Cyperus es. | 8 | 8 | 10 | 8 | 10 |
| Sorghum halepense | 7 | 6 | 9 | 9 | 8 |

| | | | | | |
|---|---|---|---|---|---|
| Poa annua | 9 | 6 | 8 | 6 | 8 |
| Untreated | 10 | 10 | 10 | 10 | 10 |

EXAMPLE VIII

Cotton plants in the phase where they have 5 to 7 evolved foliage leaves were treated with the following compounds according to the invention and with a comparison compound, dispersed in 500 liters of water/ha (repeated 4 times). Three weeks after the application was completed the percentage of dropped leaves were determined. The results are set out in the following table.

| | Doses in g active agent/ha | Defoliation in % |
|---|---|---|
| Compound of the invention | | |
| 1-hydroxy-1-phenyl-3-(1,2,3-thiadiazole-5-yl)-urea | 500 | 81 |
| 1-acetoxy-1-phenyl-3-(1,2,3-thiadiazole-5-yl)-urea | 500 | 91 |
| Comparison compound | | |
| S,S,S—tri-n-butyl-trithiophosphoric acid ester | 500 | 50 |

EXAMPLE IX

Cotton plants in the stage where they have five evolved foliage leaves were treated with the compound of the invention as hereafter set out and with a comparison compound as set out in the table with the compounds dispersed in 500 liters of water/ha (repeated 4 times). Two weeks later the percentage of dropped leaves were determined. The results are set out in the following table.

| | Doses in g active agent/ha | Defoliation in % |
|---|---|---|
| Compound of the invention | | |
| 1-hydroxy-1-phenyl-3-(1,2,3-thiadiazole-5-yl)-urea | 40 | 50 |
| Comparison compound | | |
| 1-phenyl-3-(1,2,3-thiadiazole-5-yl)-urea | 40 | 40 |
| S,S,S—tri-n-butyl-trithiophosphoric acid ester | 40 | 9 |

EXAMPLE X

Cotton plants in the stage where they have 4 to 6 evolved leaves were treated with the hereinafter set out compounds of the invention and with the comparison compounds noted. The compounds were applied as the dispersion in 500 liters of water/ha (repeated 4 times). One day later the percentage of dropped leaves were determined. The results are set out in the following table.

| | Doses in g active agent/ha | Defoliation in % |
|---|---|---|
| Compound of the invention | | |
| 1-hydroxy-1-phenyl-3-(1,2,3-thiadiazole-5-yl)-urea | 500 | 90 |
| 1-acetoxy-1-phenyl-3-(1,2,3-thiadiazole-5-yl)-urea | 500 | 85 |
| 1-methoxy-1-phenyl-3-(1,2,3-thiadiazole-5-yl)-urea | 500 | 70 |
| 1-ethoxy-1-phenyl-3-(1,2,3-thiadiazole-5-yl)-urea | 500 | 75 |
| 1-methylcarbamoyloxy-1-phenyl-3-(1,2,3-thiadiazole-5-yl)-urea | 500 | 85 |
| 1-phenyl-phenylcarbamoyloxy-3-(1,2,3-thiadiazole-5-yl)-urea | 500 | 80 |
| 1-chloroacetoxy-1-phenyl-3-(1,2,3-thiadiazole-5-yl)-urea | 500 | 90 |
| 1-phenyl-1-propionyloxy-3-(1,2,3-thiadiazole-5-yl)-urea | 500 | 90 |
| 1-benzyloxy-1-phenyl-3-(1,2,3-thiadiazole-5-yl)-urea | 500 | 71.4 |
| 1-isobutyryloxy-1-phenyl-3-(1,2,3-thiadiazole-5-yl)-urea | 500 | 81.0 |
| 1-butyryloxy-1-phenyl-3-(1,2,3-thiadiazole-5-yl)-urea | 500 | 75 |
| 1-benzoyloxy-1-phenyl-3-(1,2,3-thiadiazole-5-yl)-urea | 500 | 90 |
| 1-(2-chlorobenzoyloxy)-1-phenyl-3-(1,2,3-thiadiazole-5-yl)-urea | 500 | 90 |
| 1-dimethylcarbamoyloxy-1-phenyl-3-(1,2,3-thiadiazole-5-yl)-urea | 500 | 70 |
| 1-phenyl-1-propoxy-3-(1,2,3-thiadiazole-5-yl)-urea | 500 | 70 |
| Comparison compound | | |
| 2,3-dihydro-5,6-dimethyl-1,4-dithiin-1,1,4,4-tetroxide | 500 | 10.5 |

What is claimed is:

1. A 1, 2, 3-thiadiazole-5-yl urea derivative having the formula

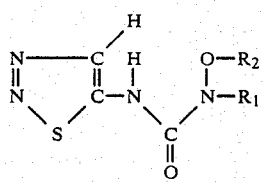

wherein $R_1$ is selected from the group consisting of phenyl, 2-chlorophenyl, 3-chlorophenyl, 4-chlorophenyl, 2-methylphenyl, 3-methylphenyl, 4-methylphenyl, 2-fluorophenyl, 2-nitrophenyl and 2-methoxyphenyl, and $R_2$ is a member selected from the group consisting of hydrogen, an alkali metal atom, an equivalent of a member selected from the group of calcium and magnesium atoms, methyl, ethyl, propyl, isopropyl, n-butyl, isobutyl, tert.-butyl, 2,2-dimethyl-1-propyl, n-pentyl, n-hexyl, 2-chloroethyl, 3-chloropropyl, 2-bromopropyl, 3-bromopropyl, 2-phenoxyethyl, 2-propenyl, 2-methyl-2-propenyl, 2-propinyl, benzyl, 2-chlorobenzyl, 3-chlorobenzyl, 4-chlorobenzyl, 3,4-dichlorobenzyl and the group

wherein $R_3$ is a member selected from the group consisting of hydrogen, methyl, ethyl, propyl, isopropyl, n-butyl, tert.-butyl, n-haphthyl, n-nonyl, n-decyl, chloromethyl, fluoromethyl, 2-chloroethyl, 1-chloroethyl, dichloromethyl, phenoxyethyl, 2-phenoxyethyl, (2,4-dichlorophenoxy)-methyl, 2-butenyl, vinyl, 2-methyl-2-propenyl, propene-1-yl, ethinyl, benzyl, 4-chlorobenzyl, cyclopropyl, cyclopentyl, cyclohexyl, methylcyclohexyl, phenyl, 3-chlorophenyl, 2-chlorophenyl, 3-methylphenyl, 4-methylphenyl, 3-nitrophenyl, 4-nitrophenyl, 2-methoxyphenyl, 4-methoxyphenyl, 1-naphthyl, 2-furyl,methoxy, ethoxy, propoxy, isopropoxy, n-butoxy, 2-propenyloxy, 2-butenyloxy, 2-propinyloxy, phenoxy, 4-chlorophenoxy, methylthio, ethylthio, propylthio, phenylthio, 4-chlorophenylthio and an amino group

wherein $R_4$ and $R_5$ are the same or different and are each selected from the group consisting of hydrogen, methyl, phenyl and 4-chlorophenyl.

2. A compound according to claim 1, designated 1-hydroxy-1-phenyl-3-(1,2,3-thiadiazole-5-yl)-urea.

3. A compound according to claim 1, designated 1-phenyl-1-propionyloxy-3-(1,2,3-thiadiazole-5-yl)-urea.

4. A compound according to claim 1, designated 1-methylcarbamoyloxy-1-phenyl-3-(1,2,3-thiadiazole-5-yl)-urea.

5. A compound according to claim 1, designated 1-methoxy-1-phenyl-3-(1,2,3-thiadiazole-5-yl)-urea.

6. A compound according to claim 1, designated 1-acetoxy-1-phenyl-3-(1,2,3-thiadiazole-5-yl)-urea.

7. A compound according to claim 1, designated 1-ethoxy-1-phenyl-3-(1,2,3-thiadiazole-5-yl)-urea.

8. A compound according to claim 1, designated 1-phenyl-1-phenylcarbamoyloxy-3-(1,2,3-thiadiazole-5-yl)-urea.

9. A compound according to claim 1, designated 1-chloroacetoxy-1-phenyl-3-(1,2,3-thiadiazole-5-yl)-urea.

10. A compound according to claim 1, designated 1-benzyloxy-1-phenyl-3-(1,2,3-thiadiazole-5-yl)-urea.

11. A compound according to claim 1, designated 1-isobutyryloxy-1-phenyl-3-(1,2,3-thiadiazole-5-yl)-urea.

12. A compound according to claim 1, designated 1-butyryloxy-1-phenyl-3-(1,2,3-thiadiazole-5-yl)-urea.

13. A compound according to claim 1, designated 1-benzoyloxy-1-phenyl-3-(1,2,3-thiadiazole-5-yl)-urea.

14. A compound according to claim 1, designated 1-(2-chlorobenzoyloxy)-1-phenyl-3-(1,2,3-thiadiazole-5-yl)-urea.

15. A compound according to claim 1, designated 1-dimethylcarbamoyloxy-1-phenyl-3-(1,2,3-thiadiazole-5-yl)-urea.

16. A compound according to claim 1, designated 1-phenyl-1-propoxy-3-(1,2,3-thiadiazole-5-yl)-urea.

17. A compound according to claim 1, designated 1-cyclopropylcarbonyl-3-phenyl-1-(1,2,3-thiadiazole-5-yl)-urea.

18. A compound according to claim 1, designated 1-(2,2-dimethylpropionyl)-3-phenyl-1-(1,2,3-thiadiazole-5-yl)-urea.

19. A compound according to claim 1, designated 1-decylcarbonyl-3-phenyl-1-(1,2,3-thiadiazole-5-yl)-urea.

20. A compound according to claim 1, designated 1-cyclohexylcarbonyl-3-phenyl-1-(1,2,3-thiadiazole-5-yl)-urea.

21. A compound according to claim 1, designated 1-formyl-3-phenyl-1-(1,2,3-thiadiazole-5-yl)-urea.

22. A plant growth regulating and defoliating agent comprising at least one compound according to claim 1.

23. A plant growth regulating and defoliating agent according to claim 22 in admixture with a suitable agricultural carrier.

24. A plant growth regulating and defoliating agent according to claim 22, additional containing at least one member selected from the group consisting of plant protection agents, pest control agents, herbicides, wetting agents, emulsifiers, solvents, surface active agents, oily additions, adhesive agents, emulsifying agents and dispersing agents.

25. A plant growth regulating and defoliating agent according to claim 22, wherein said active agent is present in an amount of from 5 to 95% by weight.

26. A method of plant growth regulation which comprises applying to the plants in an amount sufficient to produce the desired plant growth regulation a compound according to claim 1.

27. A method according to claim 26, wherein said plants are cotton.

28. A method according to claim 26, which comprises applying said active agent at the rate of 100 to 5000 liters/ha wherein said active agent is admixed with water as a carrier.

29. A method of defoliating plants which comprises applying thereto in an amount sufficient to cause defoliation a compound according to claim 1.

30. A method of defoliating plants according to claim 29, wherein said plants are cotton.

* * * * *